United States Patent [19]

Smith

[11] Patent Number: 4,977,124

[45] Date of Patent: Dec. 11, 1990

[54] CATALYST COMPOSITION FOR COUPLING PROCESS

[75] Inventor: R. Scott Smith, Baton Rouge, La.

[73] Assignee: Ethyl Corporation, Richmond, Va.

[21] Appl. No.: 374,043

[22] Filed: Jun. 30, 1989

[51] Int. Cl.$^5$ ...................... B01J 23/02; B01J 27/232
[52] U.S. Cl. .................................... 502/174; 502/340; 502/341; 502/344; 585/452
[58] Field of Search ............... 502/174, 340, 341, 344; 585/452

[56] References Cited

U.S. PATENT DOCUMENTS 3,291,847 12/1966 Warner ............................... 585/452
4,511,748 4/1985 Kudoh et al. ................... 502/344 X Primary Examiner—W. J. Shine
Attorney, Agent, or Firm—Patricia J. Hogan; Richard J. Hammond

[57] ABSTRACT

A catalyst composition having enhanced effectiveness in coupling an alkene with an aromatic hydrocarbon having an active hydrogen on a saturated α-carbon is obtained by dispersing an alkali metal onto a supported oxide of sodium, potassium, rubidium, cesium, barium, strontium, calcium, or magnesium in the absence of a diluent.

9 Claims, No Drawings

CATALYST COMPOSITION FOR COUPLING PROCESS

FIELD OF INVENTION

This invention relates to catalyst compositions and more particularly to catalyst compositions which can be used in the coupling of alkenes with aromatic hydrocarbons having an active hydrogen on a saturated α-carbon.

BACKGROUND

U.S. Pat. No. 4,179,580 (Cobb), European Pat. No. 128001 (Kudoh et al.), and Eberhardt et al., *Journal of Organic Chemistry*, Vol. 30, pp. 82–84 (1965) show that it is known that supported alkali metals are useful as catalysts in the coupling of ethylenically-unsaturated hydrocarbons with aromatic hydrocarbons having an active hydrogen on a saturated α-carbon. The supported alkali metals are more effective than the corresponding unsupported alkali metals in such reactions but are still not as effective as might be desired.

As disclosed in copending applications Ser. No. 135,318 (Smith), filed Dec. 21, 1987, now abandoned, and 276,531 (Smith), 276,532 (Smith), and 276,533 (Smith), filed Nov. 28, 1988, now abandoned, it has been found that alkenes can advantageously be coupled with aromatic hydrocarbons having an active hydrogen on a saturated α-carbon in the presence of a supported alkali metal as a catalyst and about 10–100 mol %, based on the amount of the alkali metal catalyst, of an oxide of sodium, potassium, rubidium, cesium, barium, strontium, calcium, or magnesium as a co-catalyst. However, it has also been found that inferior results are obtained when the catalyst system is prepared in the conventional manner, i.e., by dispersing the alkali metal onto a mixture of the support and the oxide in the presence of a diluent.

SUMMARY OF INVENTION

An object of this invention is to provide a novel catalyst composition.

Another object is to provide such a composition which has increased effectiveness in catalyzing the coupling of an alkene with an aromatic hydrocarbon having an active hydrogen on a saturated α-carbon.

These and other objects are attained by dispersing an alkali metal onto a supported oxide of sodium, potassium, rubidium, cesium, barium, strontium, calcium, or magnesium in the absence of a diluent.

DETAILED DESCRIPTION

The alkali metal employed in the practice of the invention may be lithium, sodium, potassium, rubidium, or cesium; and it appropriately has its surface area increased by being finely divided or liquid as well as by being supported on the alumina. It is preferably potassium or a potassium alloy, e.g., NaK.

The support employed may be any suitable support material, such as diatomaceous earth, activated charcoal, granular coke, silica, alumina, pumice, porcelain, quartz, steel turnings, copper shot, sodium carbonate, potassium carbonate, etc.; but it is preferably a support, such as alumina or sodium carbonate, having a relatively small surface area, i.e., not greater than about 10 $m^2/g$.

The oxide, like the alkali metal, is used in finely-divided form. It may be combined with the support by simple physical admixture, but it is preferably introduced by dispersing on the support the alkali or alkaline earth metal corresponding to the desired oxide and oxidizing the metal by known techniques. The amount utilized is such as to provide about 10–100 mol % of the oxide, based on the amount of the alkali metal. Ordinarily, the preferred oxide is sodium oxide.

When the novel catalyst composition is employed in a coupling reaction, it is used in an amount such as to provide a catalytic amount of the alkali metal, generally about 2–10 mol %, based on the amount of either of the reactants when they are utilized in equimolar amounts or on the amount of the major reactant when they are not utilized in equimolar amounts.

As in the processes of Smith, the alkene which is coupled with the aromatic hydrocarbon in the presence of the catalyst composition may be any of the alkenes which are known to be useful in such reactions, such as ethene, propene, 1-butene, 2-butene, isobutene, 1-pentene, 2-pentene, 3-methyl-1-butene, 2-methyl-2-butene, 1-hexene, 2-hexene, 3-hexene, 4-methyl-1pentene, 3-methyl-1-pentene, 4-methyl-2-pentene, 1-heptene, 2-heptene, 2-octene, 4-nonene, 1-decene, 2-decene, 1-dodecene, 3-tetradecene, 5-hexadecene, 6-methyl-4-heptadecene, 1-eicosene, etc. However, it is generally an alkene corresponding to the formula QQ'C=CTT', in which Q, Q', T, and T' are independently selected from hydrogen and alkyl groups of up to 20 carbons; and it is apt preferably to be an alkene of up to 20 carbons. Particularly preferred alkenes are ethene and propene.

The aromatic hydrocarbon having an active hydrogen on a saturated α-carbon may be any such compound that is known to be useful in such reactions, such as toluene, ethylbenzene, n-propylbenzene, isopropylbenzene, n-butylbenzene, sec-butylbenzene, isobutylbenzene, n-eicosylbenzene, o-, m-, and p-xylenes, o-, m-, and p-ethyltoluenes, 1,3,5-trimethylbenzene, 1,2,3,4- and 1,2,3,5-tetramethylbenzenes, p-diisopropylbenzene, 1- and 2-methylnaphthalenes, dimethylnaphthalenes, 1-ethyl-4-n-octadecylnaphthalene, 1,4-di-n-pentylnaphthalene, 1,2,3,4-tetrahydronaphthalene, indan, cyclohexylbenzene, methylcyclohexylbenzene, diphenylmethane, etc. However, it is generally a hydrocarbon corresponding to the formula RR'R"CH, in which R is an aryl group of up to 20 carbons and R' and R" are independently selected from hydrogen and alkyl and aryl groups of up to 20 carbons; and it is apt preferably to be an alkylbenzene having one or more ar-alkyl groups. A particularly preferred aromatic hydrocarbon is toluene.

The mol ratio of alkene to aromatic hydrocarbon in these coupling reactions varies with the particular reactants employed and the products desired, particularly since the aromatic hydrocarbon may have one or more active hydrogens, and it may be desired to react the alkene with only one or with more than one active hydrogen in the aromatic hydrocarbon. It is frequently preferred to employ the reactants in the stoichiometric amounts appropriate for the preparation of the desired product. However, either reactant can be used in excess.

The coupling reaction is conducted by heating a mixture of the alkene, the active hydrogen-containing aromatic hydrocarbon, and the novel catalyst composition under substantially anhydrous conditions at a suitable temperature, generally about 100–300° C., preferably about 175–200° C., to couple the reactants. It is generally conducted in the absence of a diluent or in the presence of an excess of the active hydrogen-containing aromatic hydrocarbon as the sole diluent. However, an inert diluent can be used if desired. Exemplary of such diluents are liquid alkanes, cycloalkanes, and aromatic hydrocarbons, such as pentane, hexane, isooctane, cyclohexane, naphthalene, decahydronaphthalene, white oils, etc.

The catalyst compositions of the invention are advantageous in that they provide faster reaction rates and higher product yields in coupling reactions than comparable catalyst compositions prepared by dispersing the alkali metal onto the alumina in the presence of a diluent. The coupling reactions in which they are used are particularly advantageous as a means of alkylating alkylaromatic compounds, especially alkylbenzenes, to form compounds useful as solvents, internal standards, intermediates for polymers, pharmaceuticals, or pesticides, etc.

The following examples are given to illustrate the invention and are not intended as a limitation thereof.

COMPARATIVE EXAMPLE A

A suitable reaction vessel was sequentially charged with 10 g of alumina having a surface area of 4 m²/g, 92 g of toluene, and 1.0 g of NaK (an alloy having a K content of 78% by weight). The mixture was stirred and heated to 185° C., after which propene was charged until a pressure of 400 psig was reached. During the reaction the stirrer was stopped periodically to allow the solids to settle; and samples were drawn, allowed to cool to room temperature, and subjected to GC analysis to determine the amounts of unreacted toluene, desired isobutylbenzene (IBB) product, and n-butylbenzene (NBB) and methylindan (MI) by-products. The results of the analyses are shown below.

| Time (min.) | Mols × 100 | | | |
| --- | --- | --- | --- | --- |
| | Toluene | IBB | NBB | MI |
| 40 | 81.1 | 11.1 | 0.43 | 3.66 |
| 120 | 62.1 | 21.9 | 0.89 | 6.55 |
| 200 | 54.5 | 25.1 | 1.01 | 7.13 |
| 240 | 53.2 | 25.5 | 1.04 | 7.18 |

COMPARATIVE EXAMPLE B

Comparative Example A was repeated except that 0.26 g of −325 mesh powdered sodium oxide was charged to the reaction vessel after the charging of the alumina. The results of the analyses are shown below.

| Time (min.) | Mols × 100 | | | |
| --- | --- | --- | --- | --- |
| | Toluene | IBB | NBB | MI |
| 40 | 99.8 | 0.4 | 0.04 | 0 |
| 120 | 82.8 | 8.4 | 1.09 | 0.14 |
| 200 | 48.5 | 34.8 | 4.19 | 0.50 |
| 240 | 33.1 | 45.8 | 5.33 | 0.54 |

EXAMPLE I

Comparative Example B was essentially repeated except that the catalyst composition was performed by charging 10 g of the alumina having a surface area of 4 m²/g and 0.26 g of −325 mesh sodium oxide to a suitable vessel, degassing the alumina under vacuum to remove traces of oxygen, filling the flask with nitrogen, adding 1.0 g of NaK at room temperature, and stirring the mixture until a blue free-flowing powder was obtained. The analytical results are shown below.

| Time (min.) | Mols × 100 | | | |
| --- | --- | --- | --- | --- |
| | Toluene | IBB | NBB | MI |
| 40 | 82.2 | 15.1 | 1.95 | 0.19 |
| 120 | 44.2 | 48.4 | 5.41 | 0.27 |
| 200 | 26.6 | 63.2 | 6.25 | 0.25 |

EXAMPLE II

Example I was essentially repeated except that the reaction temperature was 160° C. instead of 185° C. The analytical results are shown below.

| Time (min.) | Mols × 100 | | | |
| --- | --- | --- | --- | --- |
| | Toluene | IBB | NBB | MI |
| 40 | 98.8 | 1.2 | 0.15 | 0 |
| 120 | 83.1 | 11.7 | 1.49 | 0.12 |
| 200 | 64.9 | 26.2 | 3.3 | 0.22 |

EXAMPLE III

Example II was essentially repeated except that, prior to the addition of the NaK, the supported sodium oxide was prepared in situ by adding 0.6 g of fresh-cut sodium metal to 25 g of the alumina, heating the mixture to 140° C. under nitrogen with stirring to disperse the sodium onto the alumina and form a gray-blue powder, heating the powder to 160° C. with stirring, passing 5 mol % oxygen in nitrogen through the flask for one hour at a rate of 0.25 standard liter per minute, cooling the gray-white powder thus obtained to room temperature under nitrogen, and analyzing a sample to determine the amount of sodium metal converted. The results showed only 5% of the sodium metal remained unreacted.

The results of analyses of the coupling reaction samples are shown below.

| Time (min.) | Mols × 100 | | | |
| --- | --- | --- | --- | --- |
| | Toluene | IBB | NBB | MI |
| 40 | 93.8 | 4.9 | 0.61 | 0.04 |
| 120 | 72.3 | 23.8 | 3.00 | 0.13 |
| 200 | 57.2 | 37.8 | 4.70 | 0.08 |

EXAMPLE IV

Example III was essentially repeated except that the supported sodium oxide that was mixed with the NaK in the absence of the diluent was 15.5 g of the material obtained by stirring 1.3 g of freshly cut sodium metal with 37.5 g of dried, granular sodium carbonate having a surface area of less than 1.0 m²/g for 30 minutes at 140° C. under nitrogen, increasing the temperature to 160° C., passing 5 mol % oxygen in nitrogen through the flask for one hour at a rate of 0.25 standard liter per minute, and cooling and degassing the resulting powder. The results of analyses of the coupling reaction samples are shown below.

| Time (min.) | Mols × 100 | | | |
| --- | --- | --- | --- | --- |
| | Toluene | IBB | NBB | MI |
| 60 | 89 | 9.0 | 1.11 | 0.08 |

-continued

| Time (min.) | Mols × 100 | | | |
| --- | --- | --- | --- | --- |
| | Toluene | IBB | NBB | MI |
| 120 | 74 | 22.7 | 2.79 | 0.16 |
| 260 | 52.2 | 41.7 | 5.07 | 0.24 |

It is obvious that many variations may be made in the products and processes set forth above without departing from the spirit and scope of this invention.

What is claimed is:

1. A catalyst composition prepared by dispersing potassium or a sodium potassium alloy onto a supported oxide of sodium, potassium, rubidium, cesium, barium, strontium, calcium, or magnesium in the absence of a diluent.

2. The composition of claim 1 wherein the alkali metal is NaK.

3. The composition of claim 1 wherein the oxide is sodium oxide.

4. The composition of claim 1 wherein the support is an alumina having a surface area not greater than about 10 $m^2/g$.

5. The composition of claim 1 wherein the support is a sodium carbonate having a surface area not greater than about 10 $m^2g$.

6. The composition of claim 1 wherein the supported oxide is obtained by dispersing the alkali or alkaline earth metal corresponding to the oxide on the support and oxidizing it.

7. The composition of claim 1 wherein the alkali metal and the oxide are employed in such amounts as to provide about 10–100 mol % of the oxide, based on the amount of the alkali metal.

8. The composition of claim 1 which is prepared by dispersing 0.1–1 molar proportion of sodium on an alumina having a surface area not greater than about 10 $m^2/g$, oxidizing the sodium to sodium oxide, and dispersing one molar proportion of NaK onto the resultant alumina-supported sodium oxide in the absence of a diluent.

9. The composition of claim 1 which is prepared by dispersing 0.1–1 molar proportion of sodium on a sodium carbonate having a surface area not greater than about 10 $m^2/g$, oxidizing the sodium to sodium oxide, and dispersing one molar proportion of NaK onto the resultant sodium carbonate-supported sodium oxide in the absence of a diluent.

* * * * *